(12) United States Patent
Kodama

(10) Patent No.: US 8,007,108 B2
(45) Date of Patent: Aug. 30, 2011

(54) IMAGE PROCESSING APPARATUS AND METHOD OF CONTROLLING IMAGE PROCESSING APPARATUS

(75) Inventor: Taku Kodama, Kawasaki (JP)

(73) Assignee: Ricoh Company Limited, Tokyo (JP)

( * ) Notice: Subject to any disclaimer, the term of this patent is extended or adjusted under 35 U.S.C. 154(b) by 122 days.

(21) Appl. No.: 12/534,522

(22) Filed: Aug. 3, 2009

(65) Prior Publication Data

US 2010/0033679 A1 Feb. 11, 2010

(30) Foreign Application Priority Data

Aug. 8, 2008 (JP) ................................. 2008-205842

(51) Int. Cl.
*A61B 3/06* (2006.01)
(52) U.S. Cl. .............................................. 351/242
(58) Field of Classification Search ................. 351/242, 351/246, 222
See application file for complete search history.

(56) References Cited

U.S. PATENT DOCUMENTS

| | | | |
|---|---|---|---|
| 5,297,559 A * | 3/1994 | Severns | 600/558 |
| 6,985,524 B1 * | 1/2006 | Borchers | 375/240 |
| 7,264,356 B2 * | 9/2007 | Jones et al. | 351/242 |
| 7,379,586 B2 * | 5/2008 | Ohashi et al. | 382/162 |
| 2005/0105796 A1 * | 5/2005 | Hong et al. | 382/162 |
| 2007/0236656 A1 * | 10/2007 | Jeong et al. | 351/163 |

FOREIGN PATENT DOCUMENTS

| | | |
|---|---|---|
| JP | 2000-181426 | 6/2000 |
| JP | 2002-248096 | 9/2002 |
| JP | 2004-94814 | 3/2004 |
| JP | 2006-246072 | 9/2006 |
| JP | 2007-190113 | 8/2007 |
| JP | 2007-232859 | 9/2007 |
| JP | 2008-42517 | 2/2008 |

OTHER PUBLICATIONS

"Color Univeral Design", Color Universal Design Organization, http://cudo.jp/e/.

* cited by examiner

*Primary Examiner* — Hung X Dang

(74) *Attorney, Agent, or Firm* — Oblon, Spivak, McClelland, Maier & Neustadt, L.L.P.

(57) ABSTRACT

An image processing apparatus includes an operation device and a color vision type detector. The operation device receives a user instruction input by a user, which indicates the selection of at least one of a plurality of processing functions to be applied onto image data by the image processing apparatus. The color vision type detector determines a color vision type of the user who inputs the user instruction based on the selection of at least one of the plurality of processing functions obtainable from the user instruction.

16 Claims, 3 Drawing Sheets

IMAGE PROCESSING APPARATUS AND METHOD OF CONTROLLING IMAGE PROCESSING APPARATUS

CROSS-REFERENCE TO RELATED APPLICATIONS

This patent application is based on and claims priority under 35 U.S.C. §119 to Japanese Patent Application No. 2008-205842, filed on Aug. 8, 2008, in the Japanese Patent Office, the disclosure of which is hereby incorporated herein by reference.

FIELD OF THE INVENTION

The present invention generally relates to an apparatus, method, computer program and product, each capable of displaying information to users having various types of color vision.

BACKGROUND

With the recent development in color image output technology such as the technology to display or output a color image, various documents or data such as a webpage created by an individual or a corporation are generated with characters or graphical images of many different colors. In one example, the characters may be displayed in color in order to notify a viewer of the document of the importance of information conveyed by the characters displayed in color. In another example, the data illustrated in a graph may be displayed in different colors in order to notify a viewer of the document that these data belong to different groups. In order to accurately interpret the information included in such document produced in color, the viewer is expected to accurately recognize the differences in color as well as the characters and the images.

For example, if the viewer happens to be a person with color vision defects who sees the color differently from ordinary people, the viewer may not correctly recognize information conveyed by the color. For example, if the person has difficulty in detecting the red color and the green color, the person may only recognize information in the blue color if the graph provides information in red, green, and blue colors.

According to the recent physiological and medical research related to the human vision, various color vision defect types are known including the red-green color blindness, the yellow-blue color blindness, and the total color blindness. According to the Color Universal Design Organization (CUDO), the human vision types can be classified into various types including the Common type (C-type), the Protanopia type (P-type) such as the strong Protanopia and the weak Protanopia, Deuteranopia type (D-type) such as the strong Deuteranopia type and the weak Deuteranopia type, Tritanopia type (T-type), and Achromatopia type (A-type). The person with the C-type vision is the person with the ordinary color vision, while the person with the other type vision is the person with the color vision defects.

In order to accurately convey information to those who may have the color vision defects, the original colors of the information may be converted to the colors that can be easily recognized by a person with the color vision defects when a request is received from the person with the color vision defects, for example, as described in the Japanese Patent Application Publication Nos. 2002-248096, 2000-181426, and 2006-246072.

SUMMARY

While the technology described in the above-described patent publications is capable of displaying the information in the colors that can be easily recognized by the person with the color vision defects, the person with the color vision defects is still required to input the request for converting, which may be cumbersome especially for the person with the color vision defects. Further, if the person with the color vision defects inputs such request for converting, the other users may know that the person who has input such request for converting has the color vision defects. Further, the person with the color vision defects himself or herself may be reminded of the fact that he or she has the color vision defects every time the person inputs such request for converting.

In view of the above, the inventor of the present invention has discovered that there is a need for an apparatus that not only displays various information in a manner that the person with the color vision defects can easily recognize, but also displays various information in a manner that any person who uses the apparatus does not instantly realize that the apparatus is specially designed for the person with the color vision defects. Further, the inventor of the present invention has discovered that there is a need for an apparatus that not only displays various information in a manner that the person with the color vision defects can easily recognize, but also displays various information in a manner that even the person with the color vision defects does not realize that the person has the color vision defects when using the apparatus.

Example embodiments of the present invention include an image processing apparatus including an operation device and a color vision type detector. The operation device receives a user instruction input by a user, which indicates the selection of at least one of a plurality of processing functions to be applied onto image data by the image processing apparatus. The color vision type detector determines a color vision type of the user who inputs the user instruction based on the selection of at least one of the plurality of processing functions obtainable from the user instruction.

In addition to the above-described example embodiments, the present invention may be practiced in various other ways, for example, as an image processing method, an image processing system, or a storage medium including instructions to cause a processor to perform the image processing method.

BRIEF DESCRIPTION OF THE DRAWINGS

A more complete appreciation of the disclosure and many of the attendant advantages and features thereof can be readily obtained and understood from the following detailed description with reference to the accompanying drawings, wherein.

Figure 1:
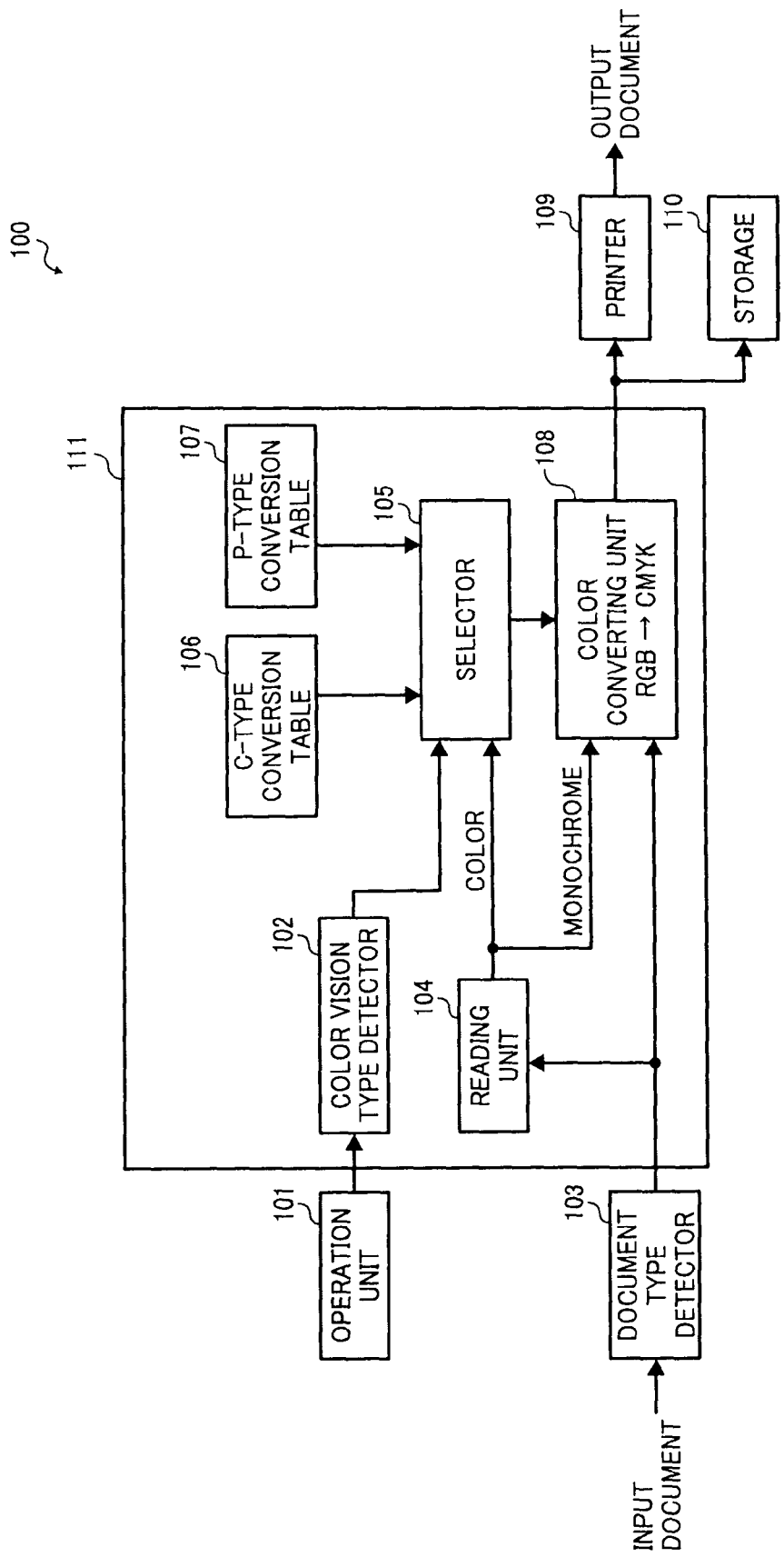
FIG. 1 is a schematic block diagram illustrating a structure of an image processing apparatus according to an example embodiment of the present invention.

The accompanying drawings are intended to depict example embodiments of the present invention and should not be interpreted to limit the scope thereof. The accompanying drawings are not to be considered as drawn to scale unless explicitly noted.

DETAILED DESCRIPTION OF EXAMPLE EMBODIMENTS

The terminology used herein is for the purpose of describing particular embodiments only and is not intended to be limiting of the present invention. As used herein, the singular forms "a", "an" and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing example embodiments shown in the drawings, specific terminology is employed for the sake of clarity. However, the present disclosure is not intended to be limited to the specific terminology so selected and it is to be understood that each specific element includes all technical equivalents that operate in a similar manner.

Referring now to FIG. 1, a structure of an image processing apparatus 100 is explained according to an example embodiment of the present invention. The image processing apparatus 100 includes an operation unit 101, a color vision type detector 102, a reading unit 103, a document type detector 104, a selector 105, a C-type color conversion table 106, a P-type color conversion table 107, a color converting unit 108, a printer 109, and a storage device 110.

The operation unit 101 may be implemented by an input device that allows a user to input a user instruction such as a user instruction requesting the image processing apparatus 100 to perform a specific processing function, and an output device that outputs various information to the user such as one or more processing functions provided by the image processing apparatus 100. For example, the input device may be implemented by a pointing device such as a mouse, a keyboard, a microphone, any key or button, etc. The output device may be implemented by a display device such as a liquid crystal display (LCD), a speaker, etc. In this example, the operation unit 101 may be implemented by an LCD with a touch panel screen.

The color vision type detector 102 determines a color vision type of the user who inputs the user instruction through the operation unit 101, according to information obtained from the user instruction. The result of determination may be output to the selector 105.

The reading unit 103, which may be implemented by a scanner, reads an original document into image data. The reading unit 103 may be provided with an exposure glass on which the original document to be read is placed. Further, the reading unit 103 may be optionally provided with an automatic document feeder (ADF), which feeds the original document to an image reading section at which the original document that is fed is read by the reading unit 103.

The document type detector 104 determines whether the original document, or the image data, obtained by the reading unit 103 is in color or monochrome. Alternatively, the image data subjected for determination may be obtained from any other device such as the storage device 110 provided in the image processing apparatus 100 or any device outside the image processing apparatus 100. When the document type detector 104 determines that the original document is in color, the document type detector 104 may output a signal that causes the selector 105 to be activated.

The selector 105 selects either one of the C-type color conversion table 106 and the P-type color conversion table 107 based on the determination result indicating the color vision type of the user obtained from the color vision type detector 102.

The C-type color conversion table 106 includes color correspondence information, which may be used to convert a pair of pseudoisochromatic colors that can be hardly recognized by the user with the C-type color vision to a pair of colors that can be easily recognized by the user with the C-type color vision.

The P-type color conversion table 107 includes color correspondence information, which may be used to convert a pair of pseudoisochromatic colors that can be hardly recognized by the user with the P-type color vision to a pair of colors that can be easily recognized by the user with the P-type color vision.

The color converting unit 108 converts the image data, which may be obtained by the reading unit 103 or the storage device 110, from RGB image signals to CMYK image signals. At this time, the color converting unit 108 may convert any pair of pseudoisochromatic colors using selected one of the C-type color conversion table 106 and P-type color conversion table 107.

The printer 109 prints the image data of CMYK image data onto a recording sheet using a plotter provided in the printer 109.

The storage device 110 stores various data including, for example, the image data obtained by the reading unit 103 before or after conversion by the color converting unit 108, the image data obtained from the outside apparatus through a network, etc.

In this example, any one of the functions or operations provided by the color vision type detector 102, the document type detector 104, the C-type color conversion table 106, the P-type color conversion table 107, the selector 105, and the color converting unit 108 may be implemented by a controller 111, which includes a processor such as a CPU provided with a memory such as a ROM and RAM.

Figure 2:
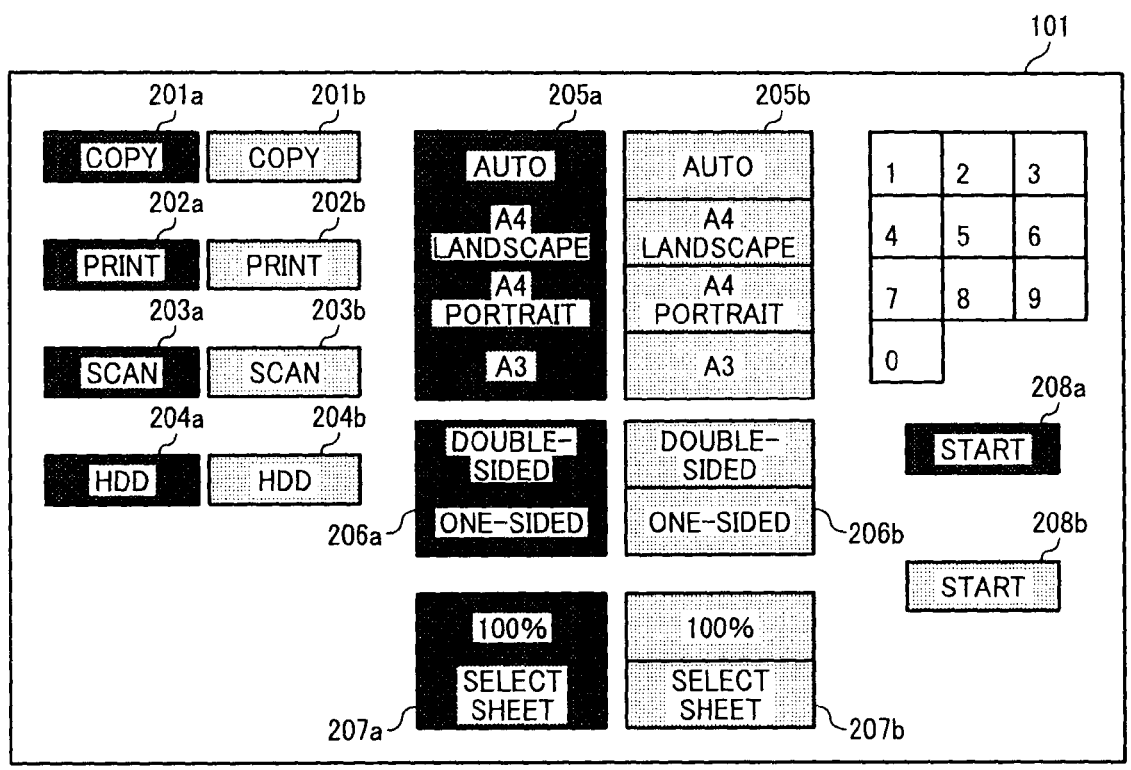
FIG. 2 is an illustration for explaining a screen displayed by the image processing apparatus illustrated in FIG. 1, according to an example embodiment of the present invention.

Referring to FIG. 2, an example screen displayed by the operation unit 101 is explained according to an example embodiment of the present invention. In this example, the screen of FIG. 2 includes a set of instruction buttons 201a to 208a designed for the C-type color vision, and a set of instruction buttons 201b to 208b designed for the P-type color vision, which are arranged side by side.

The instruction buttons 201a and 201b each allow the user to select copy operation. The instruction buttons 202a and 202b each allow the user to select printing operation. The instruction buttons 203a and 203b each allow the user to select scanning operation. The instruction buttons 204a and 204b each allow the user to select storing operation, which stores the image data in the storage device 110.

The instruction buttons 205a and 205b each allow the user to set the type of the recording sheet to be used for copying, for example, when the copying operation is selected through one of the instruction buttons 201a and 201b. More specifically, the AUTO buttons 205a and 205b each allow the user to request the image processing apparatus 100 to automatically select the recording sheet type according to the image data obtained by the reading unit 103 by reading the original document. The A4 landscape buttons 205a and 205b each allow the user to request the image processing apparatus 100 to select the recording sheet of A4 with the orientation of landscape. The A4 portrait buttons 205a and 205b each allow the user to request the image processing apparatus 100 to select the recording sheet of A4 with the orientation of portrait. The A3 buttons 205a and 205b each allow the user to request the image processing apparatus 100 to select the recording sheet of A3.

The instruction buttons 206a and 206b each allow the user to select whether the image data is to be printed on one side or both sides of the recording sheet, for example, when the copying operation is selected through one of the instruction buttons 201a and 201b. More specifically, the "double-sided" buttons 206a and 206b is selected when the user requests the image processing apparatus 100 to print the image data on the both sides of the recording sheet.

The instruction buttons 207a and 207b each allow the user to select whether to scale the image data, or the scaling ratio when the image data is to be scaled. More specifically, one of the "100%" buttons 207a and 207b is selected when the user instructs the image processing apparatus 100 to copy the original document without enlargement or reduction. One of the "SELECT SHEET" buttons 207a and 207b is selected when the user instructs the image processing apparatus 100 to print the image data onto the recording sheet having a specified sheet size after enlargement or reduction. For example, the user may instruct the image processing apparatus 100 to copy the A3 size document onto the A4 size document through the "SELECT SHEET" button 207a or 207b.

The START buttons 208a and 208b each allow the user to send the user instruction set through the screen of FIG. 2. For example, when the START buttons 208a or 208b is selected, the image processing apparatus 100 starts performing operation instructed by the user as indicated by the selection of one or more of the instruction buttons.

As illustrated in FIG. 2, a ten key may be additionally provided, which allows the user to input numerical data. Further, the type or the number of the instruction buttons to be displayed by the operation unit 101 is not limited to the above-described example of FIG. 2. The operation unit 101 may change the display of the screen according to one or more processing functions that are available for use by the image processing apparatus 100.

In this example, the C-type color vision instruction buttons 201a to 208a are each designed to be displayed with a set of colors that are easily recognizable by the person with the C-type color vision but are not easily recognizable by the person with the P-type color vision. For example, the character, such as "COPY" or "PRINT", is displayed in red, while the background color behind the character is displayed in green. The P-type color vision instruction buttons 201b to 208b are each designed to be displayed with a set of colors that are easily recognizable by the person with the P-type color vision but are not easily recognizable by the person with the C-type color vision. For example, the character, such as "COPY" or "PRINT", is displayed in dark blue, while the background color behind the character is displayed in light blue.

As described above referring to FIG. 2, as the set of buttons 201a to 208a designed for the C-type color vision, and the set of buttons 201b to 208b designed for the P-type color vision, are arranged side by side, the user at the image processing apparatus 100 does not have to concern whether the fact that the user has the color vision defects will be known by the others even when the user has the color vision defects. Further, the user, who has the color vision defects, may not even realize that the user has the color vision defects when using the image processing apparatus 100. Further, since only one waiting screen is required for display, the memory space of the image processing apparatus 100 may be efficiently used.

The example screen of FIG. 2 illustrates an example case in which the instruction buttons are prepared for each one of the C-type color vision and the P-type color vision. However, the instruction buttons designed for the P-type color vision may also function as the instruction buttons designed for the D-type color vision as the person with the D-type color vision can hardly recognize red and green colors but can easily recognize blue colors.

Alternatively, the instruction buttons may be prepared for each one of any combination or number of the color vision types. For example, in addition to the instruction buttons designed for the C-type color vision, and the instruction buttons for the P-type color vision, the screen of FIG. 2 may provide a set of instruction buttons designed for the T-type color vision. In such case, the instruction buttons for the C-type color vision is displayed in a combination of colors that are easily recognized by the user with the C-type color vision type, but are hardly recognized by the user with the P-type color vision type and the user with the T-type color vision type such as a pair of orange and green. The instruction buttons for the P-type color vision is displayed in a combination of colors that are easily recognized by the user with the P-type color vision type, but are hardly recognized by the user with the C-type color vision type and the user with the T-type color vision type such as a pair of dark blue and light blue. The instruction buttons for the T-type color vision is displayed in a combination of colors that are easily recognized by the user with the T-type color vision type, but are hardly recognized by the user with the C-type color vision type and the user with the P-type color vision type such as a pair of dark red and light red. The combination of colors may be determined based on the physiological or medical research data regarding the human vision that are available for use.

Further, in this example illustrated in FIG. 2, a plurality of the instruction buttons are prepared for each of the color vision types. Alternatively, at least one instruction button may be provided for each of the color vision types such as the START buttons 208a and 208b to determine the color vision type of the user. In such case, the instruction button that is most likely to be selected by the user widely for all processing functions may be used, such as the START buttons 208a and 208b.

However, in order to improve the accuracy in determining the color vision type of the user, more than one instruction button is provided for each one of the color vision types as illustrated in FIG. 2. Further, in such case, the color vision type detector 102 may determine the color vision type of the user based on the number of user inputs that selects the instruction buttons of specific color vision type. For example, when the user selects the instruction buttons designed for the C-type color vision repeatedly or more than a predetermined number of times, the color vision type detector 102 determines that the user has the C-type color vision.

Further, in this example illustrated in FIG. 2, the START button 208a and the START button 208b are placed in a predetermined distance from each other. This may prevent the user, who has the color vision defects, to press the START button 208a that is located by the START button 208b by mistake.

Figure 3:
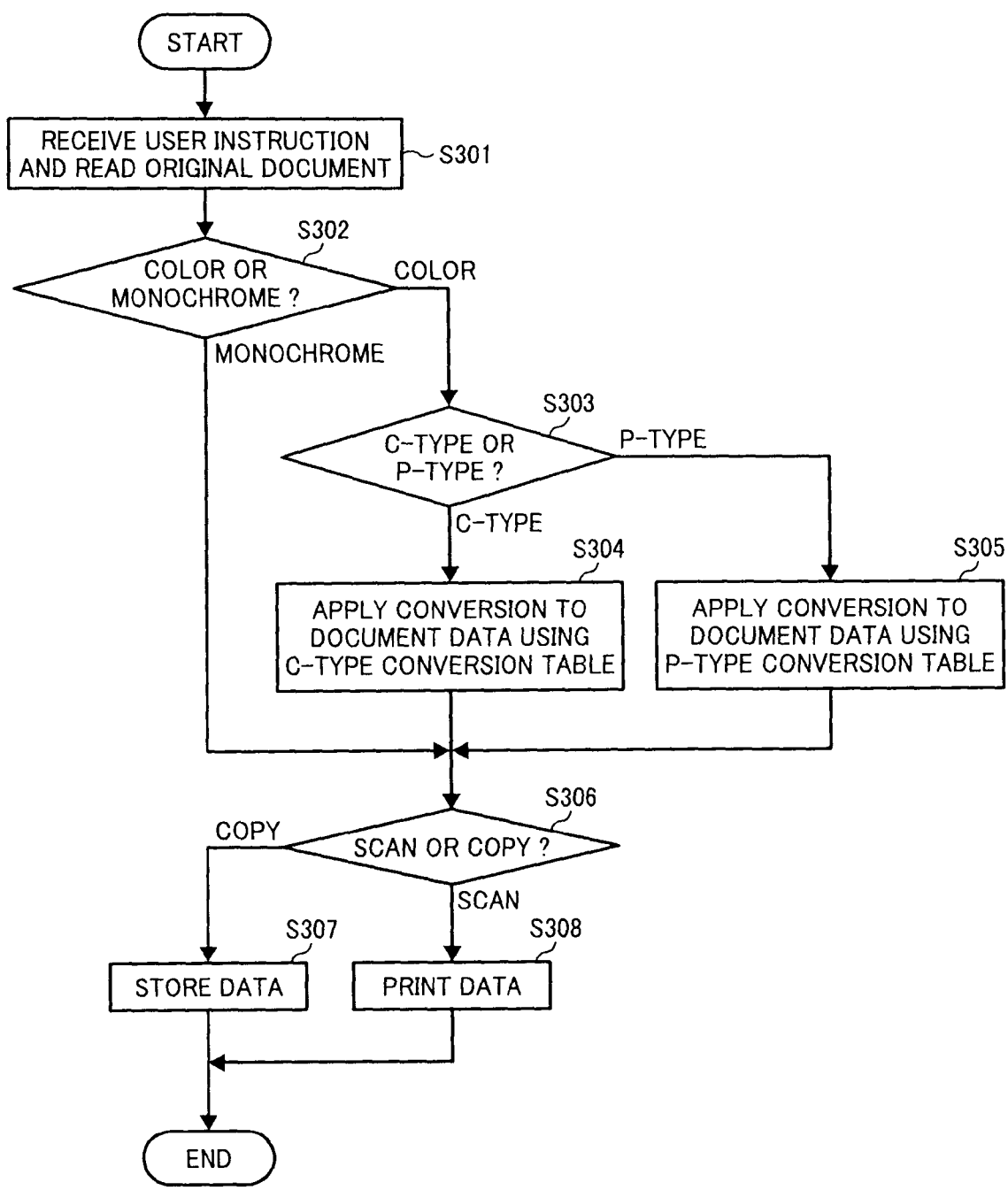
FIG. 3 is a flowchart illustrating operation of detecting a color vision type of a user and converting image data according to the detected color vision type, performed by the image processing apparatus illustrated in FIG. 1, according to an example embodiment of the present invention.

Referring to FIG. 3, operation of receiving a user instruction from a user and converting the color of an original document according to a color vision type of the user, performed by the image processing apparatus 100 of FIG. 1, is explained according to an example embodiment of the present invention. In this example, it is assumed that the user at the image processing apparatus 100 places an original document on the exposure glass of the reading unit 103 or the ADF. Further, the operation unit 101 displays the screen of FIG. 2, which includes the set of instruction buttons 201a to 208a for the C-type color vision type and the set of instruction buttons 201b to 208b for the P-type color vision type.

At S301, the image processing apparatus 100 receives a user instruction through the operation unit 101. For example, if the user intends to copy the original document, the user at least selects the COPY instruction button 201a or 201b, and the START instruction button 208a or 208b. In another example, if the user intends to scan the original document, the user at least selects the SCAN instruction button 203a or 203b, and the START instruction button 208a or 208b. When the START instruction button 208a or 208b is selected, the image processing apparatus 100 reads the original document into image data using the reading unit 103. The image data may be stored in a memory of the image processing apparatus 100.

At S302, the document type detector 104 determines whether the original document is in color or monochrome. For example, the document type detector 104 may determine whether the original document is in color or monochrome at the time of pre-scanning performed by the reading unit 103. For this reason, S301 and S302 may be performed in different orders or concurrently. When it is determined that the original document is in color such as the RGB image data ("COLOR"), the operation proceeds to S303. At this time, the selector 105 may be activated. When it is determined that the original document is in monochrome ("MONOCHROME"), the operation proceeds to S306. At this time, the selector 105 is not activated.

At S303, the color vision type detector 102 detects the color vision type of the user according to the user instruction received from the operation unit 101 at S301, which indicates the selection of at least one of the plurality of instructions buttons of FIG. 2. For example, when the selection of one or more instruction buttons designed for the C-type color vision is detected, the color vision type detector 102 determines that the user at the apparatus 100 has the C-type color vision, and outputs the detection result indicating that the user has the C-type color vision. In another example, when the selection of one or more instruction buttons designed for the P-type color vision is detected, the color vision type detector 102 determines that the user at the apparatus 100 has the P-type color vision and outputs the detection result indicating that the user has the P-type color vision. When it is determined that the user at the apparatus 100 has the C-type color vision ("C-type"), the operation proceeds to S304. When it is determined that the user at the apparatus 100 has the P-type color vision ("P-type"), the operation proceeds to S305.

More specifically, in this example, when any one of the instruction buttons designed for the C-type color vision is selected, the operation unit 101 outputs information or a signal indicating that the C-type color vision instruction button is selected. When any one of the instructions buttons designed for the P-type color vision is selected, the operation unit 101 outputs information or a signal indicating that the P-type color vision instruction button is selected. According to the signal, the color vision type detector 102 determines the color vision type of the user who inputs the user instruction to generate a detection result. The detection result may be used to select a mode of operation performed by the image processing apparatus 100.

At S304, the selector 105 selects the C-type color conversion table 106 according to the detection result output from the color vision type detector 102, and causes the color converting unit 108 to apply color conversion to the image data using the C-type color conversion table 106. As described above referring to FIG. 1, the C-type color conversion table 106 includes color correspondence information, which may be used to convert a pair of pseudoisochromatic colors that can be hardly recognized by the user with the C-type color vision to a pair of colors that can be easily recognized by the user with the C-type color vision. The color converting unit 108 applies color conversion to the image data from RGB color signals to CMYK color signals, using the C-type color conversion table 106 in addition to using a color conversion table for converting from RGB to CMYK. When one of the pseudoisochromatic color pairs of the C-type color conversion table 106 is detected in the RGB image data, the color converting unit 108 converts the detected pseudoisochromatic color pair to a color pair that can be easily recognized by the user with the C-type color vision using the color correspondence information of the C-type color conversion table 106. After conversion of the pseudoisochromatic color pair, the color converting unit 108 converts the RGB image data to the CMYK image data. Alternatively, conversion of the pseudoisochromatic color pair and the RGB-CMYK conversion may be performed concurrently.

At S305, the selector 105 selects the P-type color conversion table 107 according to the detection result output from the color vision type detector 102, and causes the color converting unit 108 to apply color conversion to the image data using the P-type color conversion table 106. As described above referring to FIG. 1, the P-type color conversion table 107 includes color correspondence information, which may be used to convert a pair of pseudoisochromatic colors that can be hardly recognized by the user with the P-type color vision to a pair of colors that can be easily recognized by the user with the P-type color vision. The color converting unit 108 applies color conversion to the image data from RGB color signals to CMYK color signals, using the P-type color conversion table 107 in addition to using the color conversion table for converting from RGB to CMYK. When one of the pseudoisochromatic color pairs of the P-type color conversion table 107 is detected in the RGB image data, the color converting unit 108 converts the detected pseudoisochromatic color pair to a color pair that can be easily recognized by the user with the P-type color vision using the color correspondence information of the P-type color conversion table 107. After conversion of the pseudoisochromatic color pair, the color converting unit 108 converts the RGB image data to the CMYK image data. Alternatively, conversion of the pseudoisochromatic color pair and the RGB-CMYK conversion may be performed concurrently.

The color conversion performed by the color converting unit 108 at S304 or S305 may be performed for each of a plurality of pixels of the image data. The pixel may correspond to 8-bit data with 256 tone levels.

At S306, the image processing apparatus 100 determines whether the user instruction input through the operation unit 101 at S301 indicates to copy or scan. When it is determined that the user instruction indicates to copy, for example, through the selection of the "COPY" button 201a or 201b ("COPY"), the operation proceeds to S307. When it is determined that the user instruction indicates to scan, for example through the selection of the "SCAN" button 203a or 203b ("SCAN"), the operation proceeds to S308.

At S307, the printer 109 prints the image data received from the color converting unit 108 onto a recording sheet, and the operation ends.

At S308, the storage device 110 stores the image data received from the color converting unit 108, and the operation ends.

As described above referring to FIG. 3, the image processing apparatus 100 is capable of automatically detecting the color vision type of the user through the selection of one of the instruction buttons displayed through the operation unit 101. Based on the detected color vision type, the image processing apparatus 100 automatically detects a section in the original document that can be hardly recognized by the user with the detected color vision type and converts the colors of the detected section to colors that can be easily recognized by the user with the detected color vision type. For example, the image processing apparatus 100 automatically detects the pseudoisochromatic color pair that can be hardly recognized by the user with the detected color vision type in the original image data, and converts the pseudoisochromatic color pair to a color pair that can be easily recognized by the user with the detected color vision type. In this manner, the original document may be printed out or stored with the colors that can be easily recognized by the user who inputs the user instruction even when the original document originally contains the color that can be hardly recognized by the user who inputs the user instruction.

In the above-described example referring to FIG. 3, the example operation of copying or scanning the original document is explained. Alternatively, the user may instruct the image processing apparatus 100 to display the image data of the original document. In such case, the color converting unit 108 applies the color conversion that converts the pseudoisochromatic color pair that can be hardly recognized by the user to the color pair that can be easily recognized by the user to generate the RGB image data for display to the user. Further, any image data stored in the storage device 110 may be transferred to another apparatus such as another image processing apparatus or a personal computer through a communication device and a network.

Alternatively, when the color vision type of the user is detected, information regarding the detected color vision type may be added to the image data obtained by the reading unit 103, and the image data having the information regarding the detector color vision type may be stored in the storage device 110 for later use. For example, the information regarding the detected color vision type may be added as property data. When the operation unit 101 receives a user instruction for outputting the image data from the storage device 110, the color vision type detector 102 detects the color vision type of a user who inputs the user instruction in a substantially similar manner as described above referring to FIG. 3. The color vision type detector 102 further compares the color vision type of the user which is detected from the user instruction with the color vision type that is attached to the image data stored in the storage device 110 to generate a comparison result. When the comparison result indicates that the color vision type that is detected matches the color vision type that is attached, the image processing apparatus 100 reads the image data from the storage device 110 and outputs the image data through the printer 109 without conversion. When the comparison result indicates that the color vision type that is detected does not match the color vision type that is attached, the image processing apparatus 100 reads the image data from the storage device 110, converts the image data using selected one of the C-type color conversion table 106 and the P-type color conversion table 107 to generate the image data having the colors that can be easily recognized by the user who inputs the user instruction.

Further, in this example, as long as the color vision type of the user who inputs the user instruction is determined, the image processing apparatus 100 may cause the operation unit 101 to display a screen in a manner that can be easily recognized by the user with the determined color vision type, for example, by providing information in the colors that can be easily recognized by the user.

In the above-described example, the image processing apparatus 100 converts the image data of the original document, which is obtained by scanning. Alternatively, the image processing apparatus 100 may select image data that is previously generated for the specific color vision type from the storage device 110. For example, various types of image data may be previously prepared for one original document, each type corresponding to one color vision type of the plurality of color vision types of the human. Based on the detection result by the color vision type detector 102, the selector 105 may select specific image data that is designed for the detected color vision type from the storage device 110, and outputs the selected image data according to a user instruction.

Alternatively, when the user at the image processing apparatus 100 can be identified, for example, using user information provided by the user at the time of logging onto the system of the image processing apparatus 100, the image processing apparatus 100 may call the detection result that is previously obtained for the logged user.

Alternatively, when the original document is provided in more than one page or more than one data file, the image processing apparatus 100 may automatically convert the subsequent pages or data files to have the colors that can be easily recognized by a user without detecting the color vision type of the user, as long as the color vision type detector 102 detects the color vision type of the user using the first page or the first data file of the original document.

Alternatively, any one of the operations or functions that can be performed by the image processing apparatus 100 of FIG. 1 may be performed by one or more apparatuses which together function as an image processing system. For example, as illustrated in FIG. 2, the functions and the operations performed by the controller 111, the operation unit 101, and the storage device 110 may be performed by a personal computer (PC) including a processor and a display device. In such case, the PC is connected to the reading unit 103 and the printer 109.

Further, any one of the above-described functions or operations may be performed by various apparatuses or systems including, for example, an image forming apparatus such as a copier, a scanner, a printer, etc., a digital camera, a portable phone with the capability of image processing, a personal assistance device, a car navigation system, etc.

Numerous additional modifications and variations are possible in light of the above teachings. It is therefore to be understood that within the scope of the appended claims, the disclosure of the present invention may be practiced otherwise than as specifically described herein.

With some embodiments of the present invention having thus been described, it will be obvious that the same may be varied in many ways. Such variations are not to be regarded as a departure from the spirit and scope of the present invention, and all such modifications are intended to be included within the scope of the present invention.

For example, elements and/or features of different illustrative embodiments may be combined with each other and/or substituted for each other within the scope of this disclosure and appended claims.

Further, as described above, any one of the above-described and other methods of the present invention may be embodied in the form of a computer program codes stored in any kind of storage medium. For example, such computer program codes may be installed onto any desired system or apparatus to cause a processor such as a CPU or a MPU of the system or the apparatus to operate as the above-described image processing apparatus 100. More specifically, when the program codes are loaded onto a memory, the processor may perform any one of the functions described above referring to FIGS. 1 to 3. Examples of storage mediums include, but are not limited to, flexible disk, hard disk, optical discs, magneto-optical discs, magnetic tapes, involatile memory cards, ROM (read-only-memory), etc. In addition to one or more of the above-described functions, execution of the program codes may cause an operating system (OS) that operates on the system or apparatus to perform at least a portion or the entire of the above-described functions according to the instructions of the program codes. Alternatively, the program codes, which may be read out from the storage medium, may be written onto a memory such as an extension board that can be optionally provided to a computer or an extension unit that can be optionally connected to a computer. After the program codes are written onto the memory, a processor such as a CPU may perform at least a portion or the entire of the above-described functions according to the instructions of the program codes. Alternatively, the computer program codes may be provided through a network, for example, from a server apparatus.

Alternatively, any one of the above-described and other methods of the present invention may be implemented by ASIC, prepared by interconnecting an appropriate network of conventional component circuits or by a combination thereof with one or more conventional general purpose microprocessors and/or signal processors programmed accordingly.

In one example, the present invention may reside in an image processing apparatus including: means for reading an original document and determining the type of the original document that is read; means for receiving a user instruction from a user for selecting at least one of a plurality of processing functions of the image processing apparatus; and means for determining a color vision type of the user based on the user instruction received by the means for receiving; means for converting the color of an image signal of the original document to the color of an image signal for output using a table that converts a pseudoisochromatic color to a color that the user can recognize that is selected based on the determined color vision type of the user when the type of the original document is determined to be a color document.

In the above-described example, the means for receiving the user instruction of the image processing apparatus includes: first means for receiving a user instruction from a user having a first color vision type; and second means for receiving a user instruction from a user having a second color vision type, which are arranged side by side for each one of the plurality of processing functions of the image processing apparatus.

In the above-described example, the first means for receiving the user instruction from the user having the first color vision type is a display section that displays information using the color that can be easily recognized by the user having the first color vision type and that can be hardly recognized by the user having the second color vision type. The second means for receiving the user instruction from the user having the second color vision type is a display section that displays information using the color that can be easily recognized by the user having the second color vision type and that can be hardly recognized by the user having the first color vision type.

In another example, the present invention may reside in a method of controlling an image processing apparatus, including: reading an original document and determining the type of the original document that is read; receiving a user instruction from a user for selecting at least one of a plurality of processing functions of the image processing apparatus; and determining a color vision type of the user based on the user instruction received by the step of receiving; converting the color of an image signal of the original document to the color of an image signal for output using a table that converts a pseudoisochromatic color to a color that the user can recognize that is selected based on the determined color vision type of the user when the type of the original document is determined to be a color document.

What is claimed is:

1. An image processing apparatus, comprising:
   an operation device configured to receive a user instruction input by a user, the operation device simultaneously displaying a plurality of image processing functions to be applied onto image data by the image processing apparatus, the user instruction indicating a selection of at least one of the functions;
   a document type detector configured to determine whether the image data is in color or monochrome;
   a color vision type detector configured to automatically determine a color vision type of the user who inputs the user instruction based on the user instruction; and
   a color converting device configured to, when the image data is determined to be in color, detect a section in the image data that includes a pseudoisochromatic color that can be hardly recognized by the user who inputs the user instruction and is assumed to have the determined color vision type, and to convert the pseudoisochromatic color of the detected section to a color that can be easily recognized by the user who inputs the user instruction and is assumed to have the determined color vision type to generate processed image data.

2. The apparatus of claim 1, wherein the display of each of the image processing functions of the image processing apparatus are divided into a plurality of instruction sections, the plurality of instruction sections including:
   a first instruction section for selection by a user with a first color vision type and corresponding to a specific one of the plurality of processing functions; and
   a second instruction section for selection by a user with a second color vision type and corresponding to the specific one of the plurality of processing functions, wherein the first instruction section and the second instruction section are arranged side by side on the display device.

3. The apparatus of claim 2, wherein alphanumeric characters of the display of each of the plurality of image processing functions of the first instruction section are identical to alphanumeric characters of the display of the plurality of image processing functions of the corresponding second instruction section.

4. The apparatus of claim 2, wherein when an image processing function in the first instruction section is selected by the user who inputs the user instruction for the specific one of the plurality of processing functions, the color vision type detector determines that the user who inputs the user instruction has the first color vision type, and
   when an image processing function in the second instruction section is selected by the user who inputs the user instruction for the specific one of the plurality of processing functions, the color vision type detector determines that the user who inputs the user instruction has the second color vision type.

5. The apparatus of claim 4, wherein the first instruction section is displayed in a color that can be easily recognized by the user with the first color vision type and that can be hardly recognized by the user with the second color vision type, and
the second instruction section is displayed in a color that can be easily recognized by the user with the second color vision type and that can be hardly recognized by the user with the first color vision type.

6. The apparatus of claim 5, further comprising:
a storage device configured to store information indicating the determined color vision type of the user who inputs the user instruction, together with the processed image data.

7. The apparatus of claim 5, wherein when the operation device receives a user instruction that is the same as the user instruction input by the user from another user, the color vision type detector is configured to obtain the processed image data from the storage device without causing the color conversion device to perform color.

8. The apparatus of claim 5, further comprising:
a first color vision type conversion table configured to store color correspondence information indicating the correspondence between a pseudoisochromatic color that can be hardly recognized by the user with the first color vision type and a color that can be easily recognized by the user with the first color vision type; and
a second color vision type conversion table configured to store color correspondence information indicating the correspondence between a pseudoisochromatic color that can be hardly recognized by the user with the second color vision type and a color that can be easily recognized by the user with the second color vision type; and
a selector configured to select one of the first color vision type conversion table and the second color vision type conversion table based on the determined color vision type of the user who inputs the user instruction, and to cause the color converting device to detect and convert the section in the image data using the color correspondence information of the selected one of the first color vision type conversion table and the second color vision type conversion table.

9. The apparatus of claim 8, wherein the color of the first instruction section is a pair of pseudoisochromatic colors that can be hardly recognized by the user with the second color vision type, and the color of the second instruction section is a pair of pseudoisochromatic colors that can be hardly recognized by the user with the first color vision type.

10. The apparatus of claim 9, wherein, when the first color vision type is the Common type and the second color vision type is the Protanopia type, the pair of pseudoisochromatic colors that can be hardly recognized by the user with the second color vision type is red and green.

11. The apparatus of claim 1, wherein the plurality of image processing functions includes at least one of start, copy, scan, HDD, sheet size, sheet orientation, sheet type, single/double sided printing, and sheet scaling.

12. An image processing method, comprising:
simultaneously displaying a plurality of image processing functions to be applied onto image data by an image processing apparatus; receiving a user instruction input by a user, the user instruction indicating a selection of at least one of the plurality of image processing functions;
determining whether the image data is in color or monochrome; and
automatically determining a color vision type of the user who inputs the user instruction based on the user instruction, wherein when the image data is determined to be in color, the method further comprising:
detecting a section in the image data that includes a pseudoisochromatic color that can be hardly recognized by the user who inputs the user instruction and is assumed to have the determined color vision type; and
converting the pseudoisochromatic color of the detected section to a color that can be easily recognized by the user who inputs the user instruction and is assumed to have the determined color vision type to generate processed image data.

13. The method of claim 12, further comprising:
dividing the display of each of the image processing functions into a plurality of instruction sections, the plurality of instruction sections including:
a first instruction section for selection by a user with a first color vision type and corresponding to a specific one of the plurality of processing functions; and
a second instruction section for selection by a user with a second color vision type and corresponding to the specific one of the plurality of processing functions, wherein the first instruction section and the second instruction section are arranged side by side on the display device.

14. The method of claim 13, wherein the first instruction section is displayed in a color that can be easily recognized by the user with the first color vision type and that can be hardly recognized by the user with the second color vision type, and
the second instruction section is displayed in a color that can be easily recognized by the user with the second color vision type and that can be hardly recognized by the user with the first color vision type.

15. The method of claim 14, further comprising:
storing, in a first color vision type conversion table, color correspondence information indicating the correspondence between a pseudoisochromatic color that can be hardly recognized by the user with the first color vision type and a color that can be easily recognized by the user with the first color vision type;
storing, in a second color vision type conversion table, color correspondence information indicating the correspondence between a pseudoisochromatic color that can be hardly recognized by the user with the second color vision type and a color that can be easily recognized by the user with the second color vision type; and
selecting one of the first color vision type conversion table and the second color vision type conversion table based on the determined color vision type of the user who inputs the user instruction, wherein the detecting and converting is performed using the color correspondence information of the selected one of the first color vision type conversion table and the second color vision type conversion table.

16. A computer readable recording medium including computer program instructions which cause a computer to execute an image processing method comprising:
simultaneously displaying a plurality of image processing functions to be applied onto image data by an image processing apparatus;
receiving a user instruction input by a user, the user instruction indicating a selection of at least one of the plurality of image processing functions;
determining whether the image data is in color or monochrome; and
automatically determining a color vision type of the user who inputs the user instruction based on the user instruction, wherein when the image data is determined to be in color, the method further comprising:

detecting a section in the image data that includes a pseudo-isochromatic color that can be hardly recognized by the user who inputs the user instruction and is assumed to have the determined color vision type; and converting the pseudoisochromatic color of the detected section to a color that can be easily recognized by the user who inputs the user instruction and is assumed to have the determined color vision type to generate processed image data.

* * * * *